United States Patent [19]

Porterfield et al.

[11] Patent Number: 4,794,916

[45] Date of Patent: Jan. 3, 1989

[54] LUMBAR STABILIZER

[76] Inventors: James A. Porterfield, 2650 Brunswick La., Hudson, Ohio 44236; Marie A. Stringer, 7108 State Rte. 14, Ravenna, Ohio 44266

[21] Appl. No.: 932,563

[22] Filed: Nov. 20, 1986

[51] Int. Cl.$^4$ .............................................. A61F 5/02
[52] U.S. Cl. ................................... 128/78; 128/101.1; 128/107.1
[58] Field of Search ...................... 128/78, 95, 99, 100, 128/101, 102, 105.1, 106.1, 89 R

[56] References Cited

U.S. PATENT DOCUMENTS

| | | | |
|---|---|---|---|
| 1,160,408 | 11/1915 | Hickok | 128/105.1 |
| 1,364,611 | 1/1921 | Cary | 128/105.1 |
| 1,542,717 | 6/1923 | Pease | 128/106.1 |
| 2,720,202 | 10/1955 | Thompson | 128/101.1 |
| 2,733,712 | 2/1956 | Wuesthoff | 128/78 |
| 3,094,984 | 6/1963 | Jewett | 128/78 |
| 3,926,183 | 12/1975 | Spiro | 128/78 |
| 3,927,665 | 12/1975 | Wax | 128/78 |
| 4,099,524 | 7/1978 | Cueman | 128/78 |
| 4,159,020 | 6/1979 | Von Soiron et al. | 128/78 |
| 4,178,923 | 12/1979 | Curlee | 128/78 |

OTHER PUBLICATIONS

PiPeer brochure entitled "Garments".
The Sports Medicine Co. brochure entitled "Lumbar Supports" Physical Therapy article entitled Waistbelt Lumbosacral Support, Robert A. Carabelli, vol. 66/No. 2, Feb. 1986, pp. 231 and 232.
IEM Orthopaedic Systems, Inc. brochure entitled "Lumbo Pelvic Support".
Bauerfeind Publication.

Primary Examiner—Robert A. Hafer
Assistant Examiner—Kevin G. Rooney
Attorney, Agent, or Firm—Renner, Kenner, Greive, Bobak, Taylor & Weber

[57] ABSTRACT

A lumbar stabilizer for the controlled displacement of tissue and application of pressure in the lumbar spine area (S) of a patient including, a belt (11) for encircling the lumbar spine area of a patient, a pair of pads (35, 35) mounted in the belt in circumferential spaced relation for positioning a distance to either side of the spinous process (84) of the lumbar spine area, a fastener (16, 17) on the belt for bringing the pair of pads into engagement with tissue in the lumbar spine area, and means (50) for selectively reducing the distance between the pair of pads to displace the tissue a distance toward the spinous process, thereby compressing and supporting the low back tissues and unloading the lumbar spine.

11 Claims, 3 Drawing Sheets

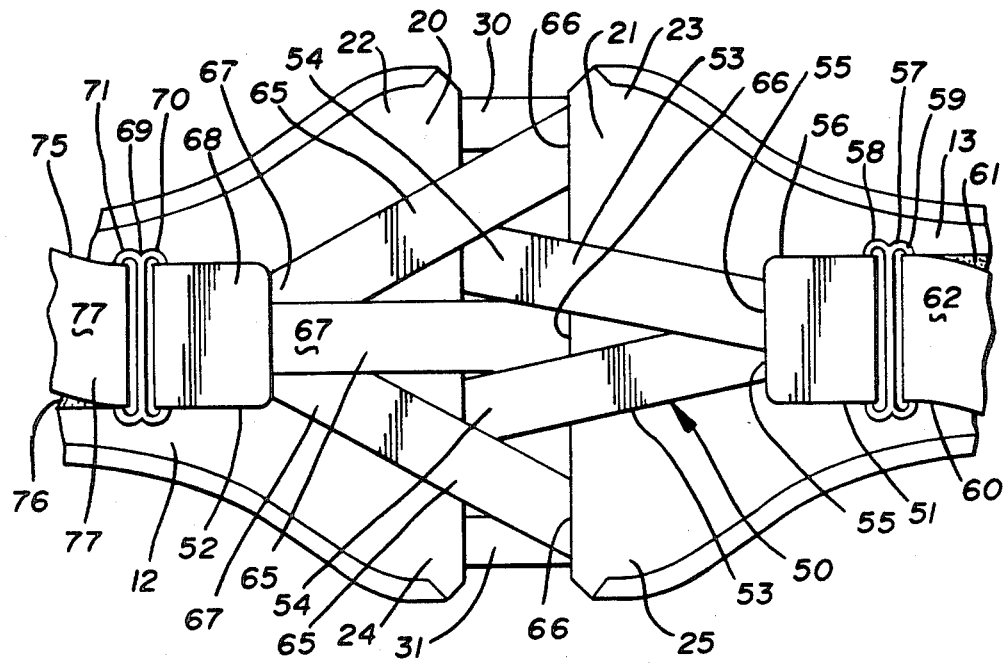
FIG. 3
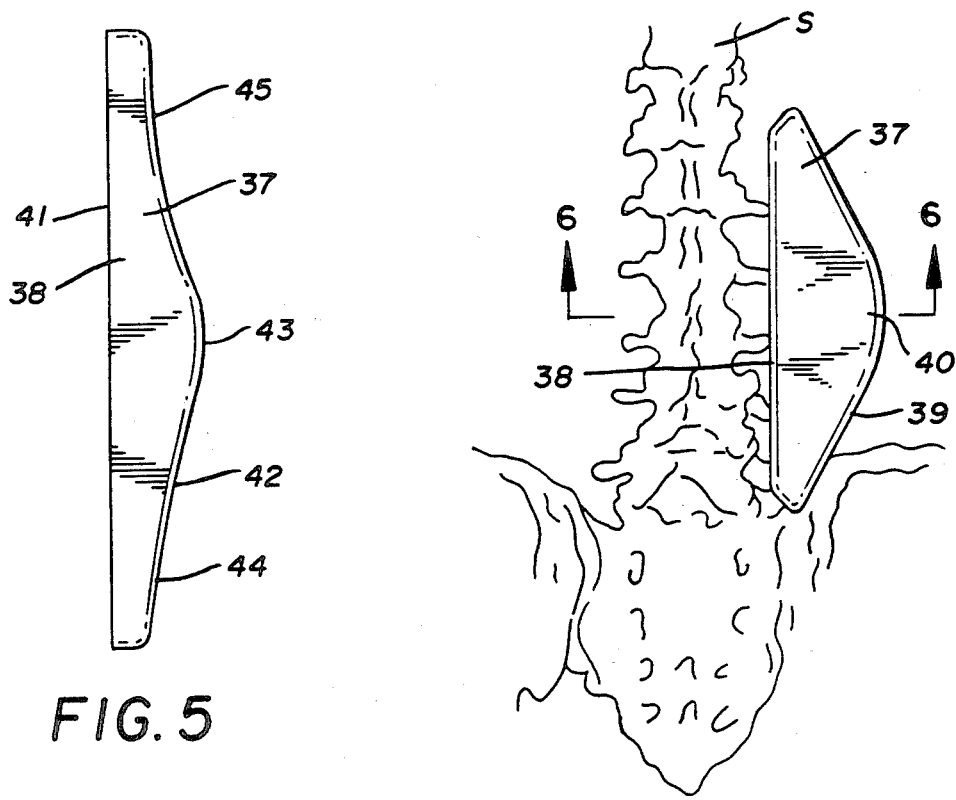
FIG. 5
FIG. 4

LUMBAR STABILIZER

TECHNICAL FIELD

The present invention relates generally to a device for temporarily supporting the lumbar region of a human being. More particularly, the present invention relates to a lumbar stabilizing device which is particularly adapted to effect controlled, nondestructive movement of lateral soft tissues in such a fashion as to configure the tissues relative to the spine such as to rest the injured region making possible functional healing.

BACKGROUND ART

Lumbar stabilizers or supports of various types have been employed for many years as a device to reduce or control both temporary and chronic discomfort located in the lower back. It is recognized that lumbar insufficiency in a broad sense is a failure of the spine to operate as a column to effect proper posture, to permit freedom of movement and to withstand work related loading. These conditions are frequently brought about as a result of weakness of the spine or muscles, inadequate exercise, loss of muscular elasticity or a lack of coordination of the muscles involved.

Lumbar stabilizers are commonly used in conjunction with conditions such as lumbar instability, disc injury, tissue sprains and strains, some lumbar fractures, and certain types of post lumbar surgery. Lumbar stabilizing devices are used both under conditions of clinical treatment and supervision and at the institution and control of individuals suffering the types of symptoms described above or perhaps recovering from conditions which at sometime in the past involved clinical treatment.

For many years lumbar stabilizers in many instances assumed generally the configuration of a corset or belt, often of exaggerated width, which were adapted to encircle a person's body in the lumbar spine area. For the most part these devices applied a uniform inward pressure of selected magnitude over the entire area and were apparently designed primarily to restrict excessive movement or activities of a person employing the device. Thus, such belts normally had little effect other than to restrict a person's activity and mobility to an extent that might tend to preclude an infliction of further damage or bring about extreme discomfort or pain.

Recently more sophisticated devices have been developed to provide support or treatment for the lumbar spine area. In this respect a common approach has been to employ some type of generally conventional waist band with an insert which is positioned in the lumbar spine area of a person. Normally, devices of this nature employ a single centrally located insert which may be oval, triangular or trapezoidal and perhaps to some extent contoured to conform to the lumbar spine area configuration of a person.

Many variations of these devices having a strategically positioned and shaped insert or pad have been introduced. In some instances these inserts may have a vertically disposed central recess which is designed to provide a relief for the spinal column and which may be of assistance in seating the insert in an optimum position relative to the lumbar spine area. Other variations of this general configuration include inserts having a firm layer of material cushioned by a softer material such as foam proximate the lumbar spine area. In other cases, thermoplastic inserts have been provided which may be heated and contoured to the lumbar spine configuration of each individual patient. In other instances, the inserts may be constructed of materials tending to restrict heat transfer such that body heat of a person in the area of the insert is maintained to a high extent when the application of heat is a desired incident to the treatment of a patient's condition. In still other instances, the insert may be provided with heating or vibratory elements which may be intermittently energized from external power sources. Yet another type of device employs an insert having a plurality of spaced knobs or projections which are directed toward the tissue of the lumbar spine area. These devices are designed to produce massage of the musculature occasioned by the constantly changing pressure distribution on the insert as a result of normal body movement.

While a great number of lumbar stabilization and treating devices have been and continue to be employed, no single device has achieved any recognized degree of superiority. A notable deficiency exists in regard to conditions which require the unloading or resting of tissues that must be controlled by nondestructive movement during the early healing stages in an injured region as part of a medically supervised rehabilitation or correction procedure.

DISCLOSURE OF THE INVENTION

Therefore an object of the present invention is to provide a lumbar stabilizer which is particularly adapted for use by a clinician to unload or rest to a controlled extent tissues of the lumbar spine area to permit functional healing. Another object of the present invention is to provide a lumbar stabilizer which selectively compresses the lateral soft tissues proximate the spine and positions them at a desired position relative to the spine to provide a controlled nondestructive movement in an injured region which permits movement while facilitating healing. Still another object of the invention is to provide a lumbar stabilizer which in thus permitting movement restores proper intratissue communication and causes osmotic pressure changes that enhance the evacuation of unwanted fluid from a damaged area, while minimizing the possibilties of deleterious disuse of tissues or reinjury thereof.

Yet another object of the invention is to provide a lumbar stabilizer which combines the interaction of specially configured padding with a specially designed pressure loading capability. Another object of the invention is to provide a lumbar stabilizer wherein the padding consists of a pair of separate padding elements which are selectively adjustable for contact with selected tissues of the lumbar spine area and for subsequent adjustment of the distance between the pads to effect selected movement of tissues initially engaged by the pads to a desired position in relation to a patient's spine elements.

Another object of the invention is to provide a lumbar stabilizer in which a plurality of separate pad members are configured for optimum tissue control in the lumbar spine region of a person. Yet another object of the invention is to provide a lumbar stabilizer having pads of varying width over the vertical length thereof to effect an advantageous grip or purchase on the tissue of the lumbar spine region. Still another object of the invention is to provide a lumbar stabilizer having a pair of pads which vary in thickness over the vertical length thereof in predetermined amounts to promote a controlled application of force to and/or movement of the tissues of the lumbar spine area. Still a further object of the invention is to provide a lumbar stabilizer which provides means for applying forces to the pads to achieve a desired resultant force of the pads on the tissues of the lumbar spine region engaged thereby.

Another object of the invention is to provide a lumbar stabilizer which is capable of being repeatedly applied with essentially the same loading conditions on the tissues of the lumbar spine area. Yet another object of the invention is to provide a lumbar stabilizer which can be applied and adjusted by a patient wearing the stabilizer or other nonclinician with a limited extent of instruction. Yet another object of the invention is to provide a lumbar stabilizer which may be relativey light weight, comfortable, nonbulky and therefore relatively inconspicuous if desired. Still a further object of the invention is to provide a lumbar stabilizer which is highly durable, strong, relatively inexpensive and can be manufactured such that a minimum number of sizes can be adjusted to fit individuals of virtually all physical characteristics.

In general, a lumbar stabilizer according to the concepts of the present invention for the controlled displacement of tissue and application of pressure in the lumbar spine area of a patient includes a belt for encircling the lumbar spine area of a patient, a pair of pads mounted in the belt in circumferential spaced relation for positioning a distance to either side of the spinous process of the lumbar spine area, a fastener on the belt for bringing the pair of pads into engagement with tissue in the lumbar spine area, and means for selectively reducing the distance between the pair of pads to displace the tissue a distance toward the spinous process, thereby compressing and supporting the low back tissues and unloading the lumbar spine.

BRIEF DESCRIPTION OF THE DRAWINGS

FIG. 3 is an elevational view of the outside of the rear portion of the lumbar stabilizer of FIG. 1 depicting particularly the adjustment system for controllably positioning the padding system relative to the lumbar tissues of a patient.

FIG. 4 is a rear elevational view of the placement of the right side pad of the padding system with the belt member removed shown in relation to a schematically depicted fragmentary portion of a spinal column of a patient on whom the lumbar stabilizer has been initially mounted.

FIG. 5 is a side elevational view of the right side pad depicted in FIG. 4.

PREFERRED EMBODIMENT FOR CARRYING OUT THE INVENTION

Figure 1:
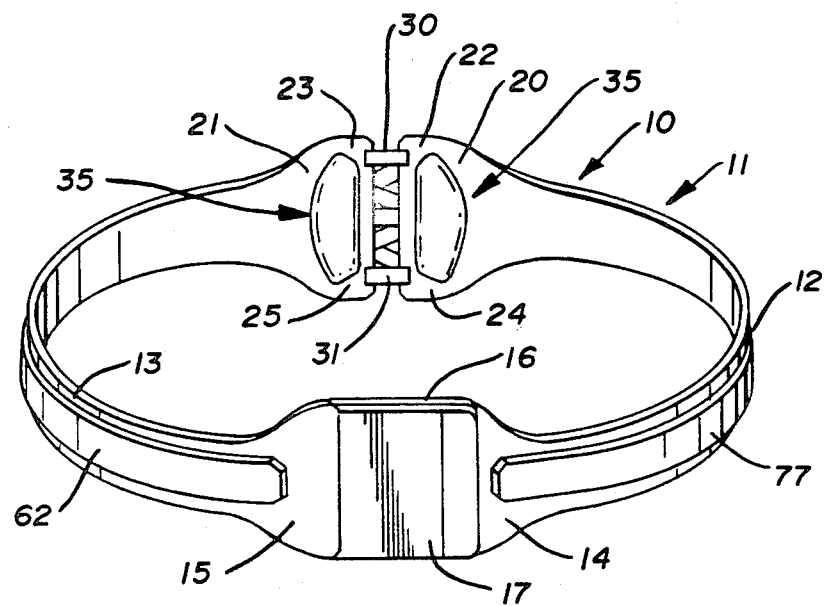
FIG. 1 is a perspective view of a lumbar stabilizer according to the concepts of the present invention and showing generally the belt member and the integrated padding system.

A lumbar stabilizer according to the concepts of the present invention is generally indicated by the numeral 10 in FIG. 1 of the drawings. As shown for exemplary purposes, the lumbar stabilizer 10 is of a generally circular configuration adapted to extend about the trunk of a person in the lumbar spine region. For ease of application and removal the lumbar stabilizer 10 may be in the nature of a belt, generally indicated by the numeral 11, of substantial width. As shown, the belt 11 is composed of two pieces, namely, a segment 12 for encircling one side of a patient and a segment 13 for encircling the other side of a patient.

The segments 12 and 13 of the belt 11 have front extremities 14 and 15, respectively, which are preferably adapted to terminate proximate the front medial portion of a person wearing the lumbar stabilizer 10 and may be of an increased width to facilitate manual manipulation. As shown, extremity 15 has a projecting tab 17 which mounts on the inner side thereof either the hook or the loop elements fasteners of a conventional VELCRO brand fastener (VELCRO is a registered trademark of Velcro, Inc.). The extremity 14 mounts on its outer surface a strip 16 containing the other of the hook or loop elements of the VELCRO fastener. Thus, the position of the extremities 14, 15 of the belt segments 12, 13 may be adjusted with respect to each other within a substantial range of variance by the positioning of the tab 17 in overlying the strip 16 circumferentially of a person wearing the lumbar stabilizer 10. While a VELCRO brand fastener is highly convenient for infinitely adjustable positioning between two members with the capability of repeated attachments and releases, it is to be appreciated that other separable fasteners could be employed in lieu thereof. For example, various types of conventional locking belt buckles, clamps, or loops could be employed for this purpose.

Figure 2:
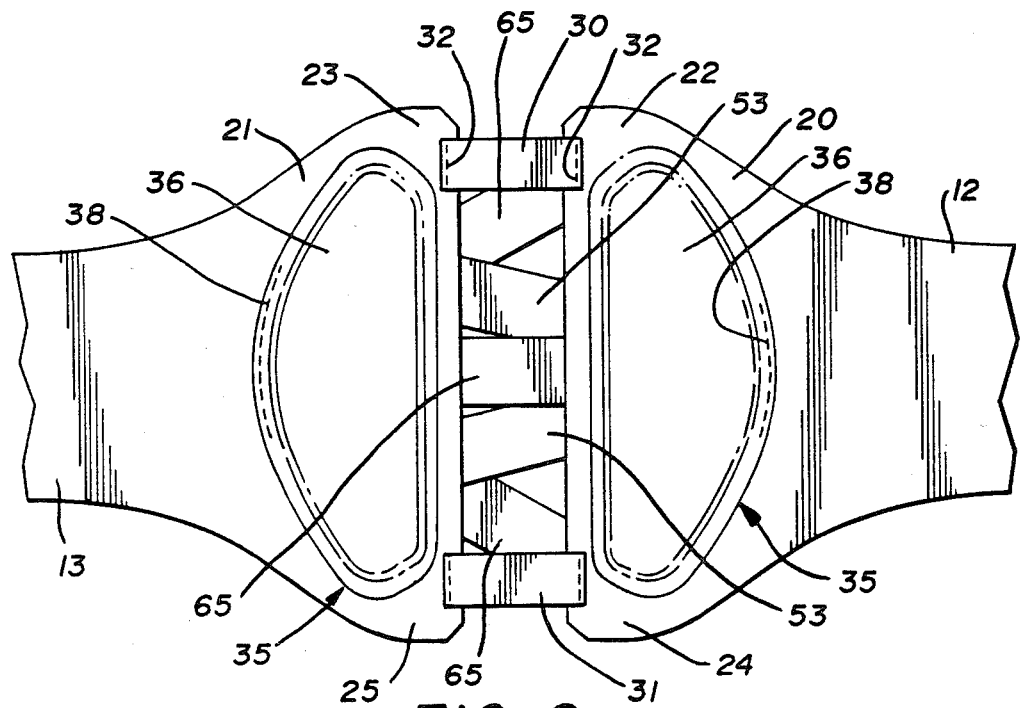
FIG. 2 is an elevational view of the inside of the rear portion of the belt member of the lumbar stabilizer of FIG. 1 showing particularly the interconnection of the two segments of the belt and the position of the integrated padding.

The belt 11 and particularly the segments 12, 13 have at the ends opposite the front extremities 14 and 15 flared rear extremities 20 and 21, respectively, as seen in FIGS. 1-3, inclusive. The flared extremities 20, 21 have top portions 22 and 23, respectively, and bottom portions 24 and 25, respectively. The belt segments 12, 13 are preferably constructed of a flexible but nonextensible material which due to the width advantageously has some breathing capability. An exemplary material having such characteristics is leather.

The flared rear extremities 20, 21 are joined to circumferentially complete segments 12 and 13 into belt 11 by connecting strips 30, 31 (FIGS. 1, 2 and 3). As shown, a pair of connecting strips 30, 31 may be employed, one joining the upper portions 22, 23 of segments 12 and 13 and the other joining the lower portions 24, 25 thereof. The strips 30, 31 are constructed of an elastic material such that, coupled with the VELCRO fastener, the belt 11 may be fastened about a patient with a controlled extent of pressure brought about by the extent of elongation of the strips 30, 31 for a purpose to be hereinafter detailed. As shown, the strips 30 are permanently affixed to the flared rear extremities 20, 21 as by stitches 31. It is to be appreciated, however, that brads, snaps, or other fasteners may be employed to effect the desired attachment.

Each of the flared rear extremities 20, 21 of belt segments 12 and 13 mount a pad assembly, generally indicated by the numeral 35. As shown each pad assembly 35 consists of a pocket 36 as seen in FIG. 2 which encompasses a pad element 37 one of which is individually depicted in FIGS. 4 and 5. The pockets 36 may consist of a piece of material, for example of the material of the belt 11, of slightly greater dimension than the length and width of the pads 37 and cut for conformance with a pad 37. The pockets 36 are attached to the flared extremities 20, 21 as by stitches 38 to permanently encase a pad 37 between the flared extremities 20, 21 and the pockets 36. While the pads 37 are configured so as to operate effectively on a range of patient waist sizes which can be feasibly handled by a particular belt size, if desired, all or a portion of the means attaching pocket 36 to flared extremities 20, 21 of the belt 22 could be temporary fasteners, such as to permit the removal and replacement of pads 37 or perhaps the substitution of pads having a slightly different size or configuration.

The preferred configuration of the pads 37 is best seen in FIGS. 4 and 5 of the drawings. As seen in FIG. 4, a pad 37 is generally rectangular and is positioned by the belt 11 so that an elongate dimension side 38 nearest the spinal column S of a patient substantially parallels the spinal column S. The pad 37 has a side 39 opposite the side 38 which is curvilinear as viewed in FIG. 4 and which has a medial portion 40 which extends outwardly to give the pad 37 a greater width medially thereof. The general positioning of the right pad 37 of a belt 11 in relation to a patient's spinal column with both the pocket 36 and flared extremity 21 of segment 13 of belt 11 removed is shown in FIG. 4 of the drawings.

The configuration of the pad 37 of FIG. 4 is further seen in FIG. 5 of the drawings. In particular, the pad 37 has a substantially planar belt engaging side 41 which is supported by the flared rear extremity 21 of the segment 13 of belt 11. The inner, pocket engaging side 42 is a curved surface which is encompassed within the pocket 36 and provides contoured support for the lumbar spine area of a patient. The inner, pocket engaging side 42 is of increased thickness at a medial portion 43 and tapers gradually to a somewhat reduced thickness portion 44 therebelow and preferably an even more reduced thickness portion 45 thereabove.

It is to be appreciated that only the pad 37 for the right side of a patient is depicted in FIGS. 4 and 5, the pad 37 for engaging the left side of a patient is essentially a mirror image of the pad 37 shown in FIG. 4, the outline of which can be seen in FIGS. 1 and 2 of the drawings. The pads 37 are preferably constructed of an elastomer which is capable of providing firm but resilient support to the tissues of a patient's lumbar spine area. More particularly, the material may be capable of undergoing some extent of distortion while having a memory which serves to continually urge contacting tissues by tending toward the original configuration of the pad 37. The elastomeric material of pad 37 may also be selected of a material which is largely unaffected by moisture, odor and other environmental conditions to which the stabilizer 10 might normally be subjected.

The two pad assemblies are positioned relative to and forces are imparted to the lumbar spine area by a strap assembly, generally indicated by the numeral 50. The strap assembly 50 consists of straps 51 and 52 as best seen in FIG. 3 of the drawings. The strap 51 has strips 53 each having one of the ends 54 attached at spaced locations at the flared rear extremity 20 of the segment 12 of belt 11. The other ends 55 of the strips 53 are attached to a loop binder 56 which is looped through a sliding clasp 57 and particularly a first ring 58 thereof. A second ring 59 of clasp 57 receives a web 60 having a portion 61 attached to the segment 13 of belt 11. The portion 61 of web 60 has on its outer face either the hook or loop elements of a VELCRO brand fastener. The web 60 also has a portion 62 which extends through the second loop 59 of clasp 57 and which may be adjustably positioned in overlapping relation to the portion 61 of web 60 such as to displace the clasp 57 and the straps 53 to the right or to the left as viewed in FIG. 3 of the drawings. The underside of the portion 62 of web 60 has the other of the hook or loop elements of a VELCRO fastener for selectively temporarily affixing the portion 62 of web 60 at any desired position relative to the portion 61 thereof.

The strap 52 of strap assembly 50 is generally similar to the above-described arrangement for strap 51. In particular, strap 52 has a plurality of strips 65 each having one of the ends 66 attached at spaced locations at the flared rear extremity 21 of segment 13 of belt 11. Thus, the spacing of the strips 65 is preferably such as to permit an intermeshing of the portions of the straps 51, 52 proximate the extremities 54, 66 such as to provide a substantially uniform transfer of force circumferentially of the belt 11.

In a manner similar to the strap 51, the strap 52 of the strap assembly 50 has ends 67 of the strips 65 which are attached to a loop binder 68 which is looped through a sliding clasp 69 which may be identical to the clasp 57. In particular, the loop binder 68 may be looped through a first ring 70 of the clasp 69. A second ring 71 of clasp 69 receives a web 75 having a portion 76 attached to the segment 12 of belt 11. The portion 76 of web 75 has on its outer face either the hook or loop elements of a VELCRO brand fastener. The web 75 also has a portion 77 which extends through the second loop 71 of clasp 69 and which may be adjustably positioned in overlapping relation to the portion 76 of web 75 such as to displace the clasp 69 and the strips 65 to the right or to the left as viewed in FIG. 3 of the drawings. The underside of portion 77 of web 75 has the other of the hook or loop elements of a VELCRO fastener for selectively temporarily affixing the portion 77 of web 75 at any desired position relative to the portion 76 thereof.

It will be appreciated that depending upon the width of the strips 53 and 65 and the width of the flared rear extremities 21, 22 of belt 11 that more or less of the straps, different widths of straps and different locations may be employed to effect the desired circumferential loading.

Figure 6:
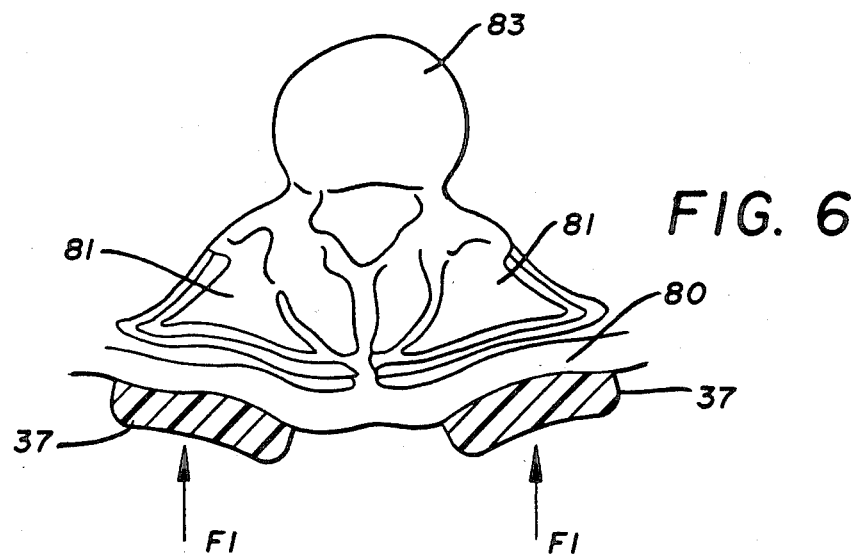
FIG. 6 is a sectional view taken substantially along the line 6—6 of FIG. 4 depicting the placement of the padding system in relation to the posterior tissues of a patient when the belt member of the lumbar stabilizer is secured about the waist of a patient.

In use, the strips 51, 52 of strap assembly 50 are normally initially unfastened such that the flared rear extremities 20 and 21 of segments 12 and 13 of belt 11 are spaced solely by the connecting strips 30, 31. The belt 11 is placed about the trunk of a patient in the lumbar spine area, and the front extremities 14 and 15 of belt 11 are joined by virtue of the fastener upon overlapping the projecting tab 17 over strip 16 such that the connecting strips 30 are slightly elongated and tensioned to bring the pad assemblies 35 into firm contact with the lumbar spine area of a patient. This initial mounting of the lumbar stabilizer 10 applies via the pads 37 forces which are directed generally as depicted as F1 in FIG. 6 of the drawings. The pads 37 apply the forces F1 to the layer of fat 80 constituting the outer layer beneath the skin of the lumbar spine area. This force is transferred into a number of lumbar structures known as erector spinae elements 81, including as will be appreciated by clinical personnel, the fascia, tendon, lumbodorsal fascia, erector spinae muscles, iliolumbar ligament, and L-1 through S-1 facet joints, which structures are often areas for treatment of the lumbar spine conditions discussed hereinabove. Interposed between the two spaced erector spinae elements 81 is the spinous process 84. Extending between the vertebrae 83 and each of the erector spinae elements 81 is the transverse process 85 which is joined with the spinous process 84 at the portion thereof proximate the vertebrae 83.

Figure 7:
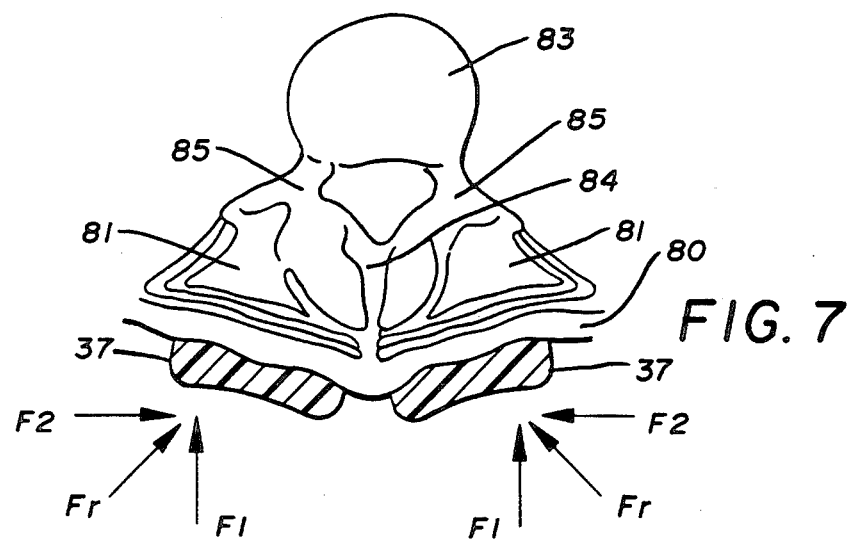
FIG. 7 is a view similar to FIG. 6 and sequential thereto depicting the application of forces by the actuation of the adjustment system, the relocation of posterior tissues and the resultant forces attained by this actuation of the adjustment system.

After the application of forces F1 by the initial mounting of the lumbar stabilizer 10 the strap assemblies 50 may have each of the straps 51 and 52 simultaneously or individually adjusted by way of tightening to apply forces generally in the direction of the forces F2 depicted in FIG. 7 of the drawings. The forces F2 as may be seen in comparing FIG. 7 with FIG. 6 displace the pads 37 to reduce the distance between the pads which tends to compress the underlying layer of fat 80 as well as the two erector spinae elements 81 which lie thereunder. The combination of the forces F1 and F2 acting on each of the pads 37 tends to produce a resultant force Fr which is directed substantially toward the juncture of the transverse process 85 with the spinous process 84 to thus maintain the lumbar spine configuration in the orientation of the components depicted in FIG. 7 and with the pads applying resultant forces Fr in the direction depicted.

In addition certain ancillary functions are accomplished as a result of the aforedescribed configuration of the pads 37. For example, the medial portion 40 of pad 37 in having a greater width places an inward force on the erector spine muscles of the erector spinae elements 81 in the mid lumbar region. Further, the reduced thickness portion 45 of the pad 37 above the medial portion 43 engages and effects a compressive force to the lumbosacral region which is believed to improve the overall effectiveness of the lumbar support 10.

Thus it should be evident that the lumbar stabilizer disclosed herein carries out the various objects of the invention set forth hereinabove and otherwise constitutes an advantageous contribution to the art. As may be apparent to persons skilled in the art, modifications can be made to the preferred embodiment disclosed herein without departing from the spirit of the invention, the scope of the invention being limited solely by the scope of the attached claims.

We claim:

1. A lumbar stabilizer for controlled displacement of tissue in the lumbar spine area of a patient comprising, belt means for encircling the lumbar spine area of a patient having two segments with a first extremity of each segment joined by connection strip means, a pair of raised pad means mounted in said first extremity of each segment of said belt means in circumferential spaced relation for positioning a distance to either side of the spinous process of the lumbar spine area, fastening means on a second extremity of each segment of said belt means for initially mounting said pair of pad means in engagement with tissue in the lumbar spine area and means for selectively reducing the distance between said first extremity of said segments and therefore said pair of pad means after said fastening means has initially mounted said pair of pad means to displace the tissue in the lumbar spine area a distance toward the spinous process, thereby compressing and supporting the low back tissues and unloading the lumbar spine, each of said pair of pad means being elongate with an inner side facing the spinous process being substantially linear, said vertically medial portion of said pads being of increased width relative to the width elsewhere along the elongate dimension of said pads to place a force on the erector spine muscles in the mid-lumbar region.

2. A lumbar stabilizer for controlled displacement of tissue in the lumbar spine area of a patient comprising, belt means for encircling the lumbar spine area of a patient having two segments with a first extremity of each segment joined by connecting strip means, a pair of raised pad means mounted in said first extremity of each segment of said belt means in circumferential spaced relation for positioning a distance to either side of the spinous process of the lumbar spine area, fastening means on a second extremity of each segment of said belt means for initially mounting said pair of pad means in engagement with tissue in the lumbar spine area, and means for selectively reducing the distance between said first extremity of said segments and therefore said pair of pad means after said fastening means has initially mounted said pair of pad means to displace the tissue in the lumbar spine area a distance toward the spinous process, thereby compressing and supporting the low back tissues and unloading the lumbar spine, each of said pair of pad means being elongate with an inner side facing the spinous process being substantially linear, said upper portion of said pads being of lesser thickness than the medial portion which engages the lumbosacral region and tends to effect an upward displacement thereof.

3. A lumbar stabilizer according to claim 2, wherein said pads have a contoured surface in facing engagement with the lumbar spine area of a patient.

4. A lumbar stabilizer for controlled displacement of tissue in the lumbar spine area of a patient comprising, belt means for encircling the lumbar spine area of a patient having two segments with a first extremity of each segment joined by connecting strip means, a pair of raised pad means mounted in said first extremity of each segment of said belt means in circumferential spaced relation for positioning a distance to either side of the spinous process of the lumbar spine area, fastening means on a second extremity of each segment of said belt means for initially mounting said pair of pad means in engagement with tissue in the lumbar spine area, am means for selectively reducing the distance between said first extremity of said segments and therefore said pair of pad means after said fastening means has initially mounted said pair of pad means to displace the tissue in the lumbar spine area a distance toward the spinous process, thereby compressing and supporting the low back tissues and unloading the lumbar spine, said pad means being constructed of an elastomeric material providing firm but resilient support to the tissue in the lumbar spine area.

5. A lumbar stabilizer according to claim 4, wherein said pair of pad means are each affixed in a pocket located in said first extremity of said two segments of said belt means.

6. A lumbar stabilizer for controlled displacement of tissue in the lumbar spine area of a patient comprising, belt means for encircling the lumbar spine area of a patient having two segments with a first extremity of each segment joined by connecting strip means, a pair of raised pad means mounted in said first extremity of each segment of said belt means in circumferential spaced relation for positioning a distance to either side of the spinous process of the lumbar spine area, fastening means on a second extremity of each segment of said belt means for initially mounting said pair of pad means in engagement with tissue in the lumbar spine area, and means for selectively reducing the distance between said first extremity of said segments and therefore said pair of pad means after said fastening means has initially mounted said pair of pad means to displace the tissue in the lumbar spine area a distance toward the spinous process, thereby compressing and supporting the low back tissues and unloading the lumbar spine, said means for selectively reducing the distance between said pair of pads including adjustable strap means attached to said first extremities of said segments of said belt means and adjustably positioned relative to the other of said segments of said belt means, said adjustable strap means including a plurality of elastic strips attached to said first extremity of said two segments of said belt means.

7. A lumbar stabilizer according to claim 6, wherein said strap means includes a web, a clasp, and fastener means for selectively adjustably tensioning said strap means and said segments and pad means controlled thereby.

8. A lumbar stabilizer according to claim 7, wherein said strap means includes a plurality of intermeshing elastic strips, some attached to each of said first extremities of said two segments of said belt means and attached by said webs to the other of said two segments of said belt means.

9. A lumbar stabilizer according to claim 8, wherein said fastener means and said means for selectively reducing the distance between said pair of pads introduces essentially normal and tangential forces to each of said pair of pad means whereby the pads assert a resultant force on the tissues of the lumbar spine area that is directed substantially toward the juncture between the spinous and transverse processes.

10. A lumbar stabilizer for controlled displacement of tissue in the lumbar spine area of a patient comprising, belt means for encircling the lumbar spine area of a patient having two segments with a first extremity of each segment joined by connecting strip means, a pair of raised pad means mounted in said first extremity of each segment of said belt means in circumferential spaced relation for positioning a distance to either side of the spinous process of the lumbar spine area, fastening means on a second extremity of each segment of said belt means for initially mounting said pair of pad means in engagement with tissue in the lumbar spine area, and means for selectively reducing the distance between said first extremity of said segments and therefore said pair of pad means after said fastening means has initially mounted said pair of pad means to displace the tissue in the lumbar spine area a distance toward the spinous process, thereby compressing and supporting the low back tissues and unloading the lumbar spine, said connecting strip means being of elastic material.

11. A lumbar stabilizer according to claim 10, wherein said connecting strip means consists of a plurality of spaced strips.

* * * * *

UNITED STATES PATENT AND TRADEMARK OFFICE
CERTIFICATE OF CORRECTION

PATENT NO.　：　　4,794,916

DATED　　　：　　January 3, 1989

INVENTOR(S) :　　James A. Porterfield and Marie A. Stringer

It is certified that error appears in the above-identified patent and that said Letters Patent is hereby corrected as shown below:

Col. 7, line 55 "connection" should read --connecting--.

Col. 8, line 47 "am" should read --and--.

Signed and Sealed this

Twenty-sixth Day of September, 1989

Attest:

DONALD J. QUIGG

Attesting Officer

Commissioner of Patents and Trademarks